US008425924B2

(12) United States Patent
Gallez

(10) Patent No.: US 8,425,924 B2
(45) Date of Patent: Apr. 23, 2013

(54) PROPYLENE COMPOSITIONS CONTAINING A PYRETHROID AND PRODUCTS MADE THEREFROM

(75) Inventor: Vincent Bernard Gallez, Ottignies-Louvain la Neuve (BE)

(73) Assignee: ExxonMobil Chemical Patents Inc., Houston, TX (US)

(*) Notice: Subject to any disclaimer, the term of this patent is extended or adjusted under 35 U.S.C. 154(b) by 198 days.

(21) Appl. No.: 12/625,290

(22) Filed: Nov. 24, 2009

(65) Prior Publication Data

US 2011/0123585 A1 May 26, 2011

(51) Int. Cl.
| | |
|---|---|
| *A01N 65/00* | (2009.01) |
| *A01N 25/08* | (2006.01) |
| *A01N 25/34* | (2006.01) |
| *A01N 29/10* | (2006.01) |
| *A01N 31/06* | (2006.01) |
| *A01N 29/02* | (2006.01) |
| *B29C 47/00* | (2006.01) |

(52) U.S. Cl.
USPC ......... 424/403; 424/405; 424/411; 264/176.1

(58) Field of Classification Search .................. 424/403, 424/411, 405
See application file for complete search history.

(56) References Cited

U.S. PATENT DOCUMENTS

| | | | |
|---|---|---|---|
| 3,248,179 | A | 4/1966 | Norwood |
| 4,241,123 | A | 12/1980 | Shih |
| 4,543,399 | A | 9/1985 | Jenkins, III et al. |
| 4,588,790 | A | 5/1986 | Jenkins, III et al. |
| 4,613,484 | A | 9/1986 | Ayres et al. |
| 5,001,205 | A | 3/1991 | Hoel |
| 5,028,670 | A | 7/1991 | Chinh et al. |
| 5,198,401 | A | 3/1993 | Turner et al. |
| 5,290,886 | A | 3/1994 | Ellul |
| 5,317,036 | A | 5/1994 | Brady, III et al. |
| 5,352,749 | A | 10/1994 | DeChellis et al. |
| 5,391,629 | A | 2/1995 | Turner et al. |
| 5,397,832 | A | 3/1995 | Ellul |
| 5,405,922 | A | 4/1995 | DeChellis et al. |
| 5,436,304 | A | 7/1995 | Griffin et al. |
| 5,453,471 | A | 9/1995 | Bernier et al. |
| 5,462,999 | A | 10/1995 | Griffin et al. |
| 5,616,661 | A | 4/1997 | Eisinger et al. |
| 5,627,242 | A | 5/1997 | Jacobsen et al. |
| 5,665,818 | A | 9/1997 | Tilston et al. |
| 5,668,228 | A | 9/1997 | Chinh et al. |
| 5,677,375 | A | 10/1997 | Rifi et al. |
| 5,693,727 | A | 12/1997 | Goode et al. |
| 5,712,352 | A | 1/1998 | Brant et al. |
| 6,881,800 | B2 | 4/2005 | Friedersdorf |
| 6,992,158 | B2 | 1/2006 | Datta et al. |
| 7,232,871 | B2 | 6/2007 | Datta et al. |
| 2005/0107530 | A1 | 5/2005 | Datta et al. |

FOREIGN PATENT DOCUMENTS

| | | |
|---|---|---|
| EP | 0 634 421 | 1/1995 |
| EP | 0 794 200 | 9/1997 |
| EP | 0 802 202 | 10/1997 |
| WO | WO 96/08520 | 3/1996 |
| WO | WO 96/33227 | 10/1996 |
| WO | WO 97/22639 | 6/1997 |
| WO | WO 00/01745 | 1/2000 |
| WO | WO 02/36651 | 5/2002 |
| WO | WO 2004/089086 | 10/2004 |
| WO | WO 2008/141928 | 11/2008 |
| WO | WO 2008/141928 A1 * | 11/2008 |
| WO | WO 2009/094027 * | 7/2009 |

OTHER PUBLICATIONS

Cheng (Polymers, Laminations, and Coatings Conference, Published 1995, pp. 71-83).*
Harper (Modern Plastics Handbook, Edited by Modern Plastics; Harper Charles A. Copyright 2004 The McGraw-Hill Companies, Chapter 4, Plastics Additives, pp. 4.1-4.70).*
J Rooney et al., "*On Line Determination by Light Scattering of Mechanical Degradation in the GPC Process*", Liquid Chromatography of Polymers and Related Materials III, J. Cazes ed., Marcel Dekker, 1981, pp. 207-235.
The Merek Index: An Encyclopedia of Chemical, Drugs, and Biologicals, $12^{th}$ ed., S. Budavari ed., 1996, p. 255.
G. Verstrate et al., "*Near Monodisperse Ethylene-Propylene Copolymers by Direct Ziegler-Natta Polymerization. Preparation, Characterization, Properties*," Macromolecules (1988) vol. 21, pp. 3360-3371.
H. N. Cheng, "*$^{13}C$ NMR Analysis of Ethylene-Propylene Rubbers,*" Macromolecules (1984) vol. 17, pp. 1950-1955.

* cited by examiner

*Primary Examiner* — Fereydoun G Sajjadi
*Assistant Examiner* — Alma Pipic

(57) ABSTRACT

Provided are compositions comprising (a) a propylene-alpha-olefin copolymer comprising at least about 50%, by weight of the propylene-alpha-olefin copolymer, of propylene-derived units and about 5% to about 35%, by weight of the propylene-alpha-olefin copolymer, of units derived from at least one of ethylene or a $C_{4-10}$ alpha-olefin, wherein the polypropylene-alpha-olefin copolymer has a heat of fusion of about 75 J/g or less, melting point of about 100° C. or less, and crystallinity of about 2% to about 65% of isotactic polypropylene; and (b) a pesticide, preferably a pyrethroid; films, filaments, fibers, sheets, molded objects, extruded articles, woven or non-woven materials, yarns, or mosquito nets made therefrom; and methods of their manufacture.

19 Claims, No Drawings

US 8,425,924 B2

PROPYLENE COMPOSITIONS CONTAINING A PYRETHROID AND PRODUCTS MADE THEREFROM

FIELD OF THE INVENTION

This invention relates to compositions having pesticidal (e.g., insecticidal, miticidal, or acardicidal) properties. More specifically, this invention relates to a composition comprising a propylene-alpha-olefin copolymer and a pesticide, methods for making the composition, and products made therefrom.

BACKGROUND OF THE INVENTION

Polymer compositions having pesticidal properties are useful for making pesticide-treated articles such as insecticide-treated nets which repel, disable, and/or kill disease-spreading insects coming into contact with these types of netting.

A conventionally treated insecticidal net is typically made by dipping the net in an insecticide. However, these nets tend to lose their insecticidal effect over time and usually require re-treating with an insecticide at least once a year or after about three washes. The World Health Organization (WHO) has issued a global guidance for the use of insecticide-treated mosquito nets to protect against malaria, and recommended that such insecticidal nets be long-lasting, i.e., retain its biological activity without re-treatment for at least 20 WHO-standard washes under laboratory conditions and 3 years of recommended use under field conditions.

A long-lasting insecticide-incorporated net, unlike conventionally treated nets, is made with a netting material having insecticide incorporated within or bound around its fibers. This can be accomplished by combining the active insecticidal ingredient with a polymer via a masterbatch to be added to a polymer base, which then can be formulated into an insecticide-incorporated fiber and subsequent product. Insecticide-incorporated nets have several advantages over conventionally treated nets. For one, having insecticide incorporated into the netting material substantially reduces the frequency of re-treatment needed. Reducing the number of re-treatments lowers costs, reduces health and safety risks associated with exposure to insecticide during re-treatment, and lessens the environmental impact. In addition, because the active insecticidal ingredient gradually and constantly migrates within the netting material to the yarn surface, insecticide-incorporated nets are expected to be effective for the entire lifetime of the net (at least three years).

Long-lasting insecticide-incorporated nets can be made starting with a masterbatch containing a pyrethroid and a polymer. WO2004/089086 relates to a composition having at least one pyrethroid and an ethylenically-unsaturated substance. The composition is said to be useful for the preparation of a premix and an insecticidal and acaricidal article of fibrous or sheet-like form with a polymeric material. The reference also describes a method for preparing the composition, premix, and the article. The composition described therein can be used as an additive for a polymeric composition in order to obtain a final material able to release an insecticidal flux. The composition is useful for the production of various articles such as fibers, mosquito nets, and other extruded items such as to films, thermo-formed or injection-molded articles.

WO2008/141928 relates to a material having insecticidal and acaricidal properties containing from 99.95% by weight to 70.0% by weight of a propylene-based polymer having a Melt Flow Rate (MFR) between 11 and 40 (ISO 1133); isotactic pentads (mmmm) higher than 90%; from 0.05% to 30% by weight of an adduct of formula T1-T2 resulting from the condensation of T1 and T2, wherein T1 comprises at least one pyrethroid substantially stable up to a temperature of at least 150° C.; T2 is an ethylenically unsaturated substance that is a surfactant, vinyl phosphate, or both. This reference states that the polypropylene-based polymer can be obtained by using a titanium and magnesium-based catalyst system or by a metallocene-based catalyst system.

There is a need for compositions containing a pesticide, e.g., a pyrethroid, and propylene-based polymer having improved processability. Propylene-alpha-olefin copolymers are a versatile thermoplastic material that can accept high filler levels and is compatible with many processing techniques. Applicant has found that when propylene-alpha-olefin copolymers are used as a carrier in a pesticidal composition, the masterbatch loading can be higher compared to when standard isotactic polypropylene is used and, furthermore, the masterbatch distribution into polypropylene matrix can be enhanced when processed under normal mixing conditions.

SUMMARY OF THE INVENTION

In one embodiment, the invention encompasses a composition comprising: (a) a propylene-alpha-olefin copolymer comprising (i) at least about 50%, by weight of the propylene-alpha-olefin copolymer, of propylene-derived units and (ii) about 5% to about 35%, by weight of the propylene-alpha-olefin copolymer, of units derived from at least one of ethylene or a $C_{4-10}$ alpha-olefin, wherein the polypropylene-alpha-olefin copolymer has a heat of fusion of about 75 J/g or less, melting point of about 100° C. or less, and crystallinity of about 2% to about 65% of isotactic polypropylene; and (b) a pesticide. Preferably, the pesticide is a pyrethroid, more preferably a condensation adduct of formula T1-T2, wherein T1 comprises at least one pyrethroid substantially stable up to a temperature of at least about 150° C. and T2 comprises an ethylenically unsaturated substance selected from at least one of a surfactant or vinyl phosphate.

The invention also encompasses a method for making a composition having pesticidal properties comprising the steps of: (1) forming a mixture comprising (a) a propylene-alpha-olefin copolymer comprising (i) at least about 50%, by weight of the propylene-alpha-olefin copolymer, of propylene-derived units and (ii) about 5% to about 35%, by weight of the propylene-alpha-olefin copolymer, of units derived from at least one of ethylene or a $C_{4-10}$ alpha-olefin, wherein the polypropylene-alpha-olefin copolymer has a heat of fusion of about 75 J/g or less, melting point of about 100° C. or less, and crystallinity of about 2% to about 65% of isotactic polypropylene; and (b) a pesticide. Preferably, the pesticide is a pyrethroid, more preferably a condensation adduct of formula T1-T2 wherein T1 comprises at least one pyrethroid substantially stable up to a temperature of at least about 150° C. and T2 comprises an ethylenically unsaturated substance selected from at least one of a surfactant or vinyl phosphate, (2) heating the mixture, and (3) extruding the mixture.

In a preferred embodiment, the method comprises the steps of: (1) forming, such as by blending, a first mixture comprising (a) a first portion of the propylene-alpha-olefin copolymer; and (b) a pesticide; (2) heating the first mixture; (3) extruding the first mixture to form a masterbatch; and (4) blending the masterbatch with a second portion of the propylene-alpha-olefin copolymer or with a polyolefin.

In one embodiment, the invention relates to a method of forming a masterbatch comprising the steps of melt blending the propylene-alpha-olefin copolymer and a pesticide, extruding the melt blend through at least one extruder die, and forming an additive masterbatch. In a preferred embodiment, the additive masterbatch comprises a polypropylene-alpha-olefin copolymer carrier, at least about 0.05%, by weight of the melt blend, of the pesticide, and preferably at least of about 0.05%, by weight of the melt blend, of at least one of a slip agent or an anti-blocking agent.

The invention also encompasses a film, filament, fiber, sheet, molded object, extruded form, woven or non-woven material, or yarn comprising any of the compositions described herein or made according to any method disclosed herein.

DETAILED DESCRIPTION OF THE INVENTION

Various specific embodiments, versions of the invention will now be described, including preferred embodiments and definitions that are adopted herein. While the following detailed description gives specific preferred embodiments, those skilled in the art will appreciate that these embodiments are exemplary only, and that the invention can be practiced in other ways. Any reference to the "invention" may refer to one or more, but not necessarily all, of the inventions defined by the claims. The use of headings is for purposes of convenience only and does not limit the scope of the invention.

The invention relates to a composition comprising a propylene-alpha-olefin copolymer and a pesticide. The propylene-alpha-olefin copolymer allows for higher filler levels when used in a masterbatch and provides for improved distribution of the masterbatch into a polymer matrix.

In one embodiment, the invention encompasses a composition comprising: (a) a propylene-alpha-olefin copolymer comprising (i) at least about 50%, by weight of the propylene-alpha-olefin copolymer, of propylene-derived units and (ii) about 5% to about 35%, by weight of the propylene-alpha-olefin copolymer, of units derived from at least one of ethylene or a $C_{4-10}$ alpha-olefin, wherein the polypropylene-alpha-olefin copolymer has a heat of fusion of about 75 J/g or less, melting point of about 100° C. or less, and crystallinity of about 2% to about 65% of isotactic polypropylene; and (b) a pesticide. Preferably, the pesticide is a pyrethroid, more preferably a condensation adduct of formula T1-T2, wherein T1 comprises at least one pyrethroid substantially stable up to a temperature of at least about 150° C. and T2 comprises an ethylenically unsaturated substance selected from at least one of a surfactant or vinyl phosphate.

In one embodiment, the composition is a masterbatch which is combined with another polymer such as a polyolefin, e.g., polypropylene, polystyrene, low density polyethylene, high density polyethylene, propylene-alpha-olefin copolymers, random copolymers of propylene with ethylene (e.g., 2-3 weight % ethylene), impact copolymers or block copolymers of polypropylene, or ethylene-propylene copolymers having, e.g., up to 20 weight % of ethylene, and formulated into an final product. Such combinations and products are also within the scope of the invention.

Propylene-Alpha-Olefin Copolymer

The propylene-alpha-olefin copolymer is a copolymer of propylene-derived units and units derived from at least one of ethylene or a $C_{4-10}$ alpha-olefin. The copolymer contains at least about 50% propylene-derived units by weight of the propylene-alpha-olefin copolymer. The propylene-alpha-olefin copolymer is a propylene-based elastomer having limited crystallinity due to adjacent isotactic propylene units and a melting point as described herein. The crystallinity and the melting point of the propylene-alpha-olefin copolymer is reduced compared to highly isotactic polypropylene by the introduction of errors in the insertion of propylene. The propylene-alpha-olefin copolymer is generally devoid of any substantial intermolecular heterogeneity in tacticity and comonomer composition, and also generally devoid of any substantial heterogeneity in intramolecular composition distribution.

The units, or comonomers, derived from at least one of ethylene or a $C_{4-10}$ alpha-olefin may be present in an amount of about 1 to about 35%, or about 5 to about 35%, preferably about 7 to about 32%, more preferably about 8 to about 25%, even more preferably about 8 to about 20%, and most preferably about 8 to about 18% by weight of the propylene-alpha-olefin copolymer. The comonomer content may be adjusted so that the propylene-alpha-olefin copolymer has a heat of fusion of about 75 J/g or less, melting point of about 100° C. or less, and crystallinity of about 2% to about 65% of isotactic polypropylene, and preferably a melt flow rate (MFR) of about 0.5 to about 90 dg/min.

The propylene-alpha-olefin copolymer may comprise more than one comonomer. Preferred embodiments of a propylene-alpha-olefin copolymer having more than one comonomer include propylene-ethylene-octene, propylene-ethylene-hexene, and propylene-ethylene-butene polymers.

In some embodiments where more than one comonomer derived from at least one of ethylene or a $C_{4-10}$ alpha-olefin is present, the amount of one comonomer may be less than about 5% by weight of the propylene-alpha-olefin copolymer, but the combined amount of comonomers by weight of the propylene-alpha-olefin copolymer is about 5% or greater.

In a preferred embodiment, the comonomer is ethylene, 1-hexene, or 1-octene, and preferably in an amount of about 5 to about 25%, about 5 to about 20%, about 5 to about 16%, about 6 to about 18%, or in some embodiments about 8 to about 20% by weight of the propylene-alpha-olefin copolymer.

In one embodiment, the propylene-alpha-olefin copolymer comprises ethylene-derived units. The propylene-alpha-olefin copolymer may comprise about 5 to about 35%, preferably about 5 to about 20%, about 10 to about 12%, or about 15 to about 20%, of ethylene-derived units by weight of the propylene-alpha-olefin copolymer. In some embodiments, the propylene-alpha-olefin copolymer consists essentially of units derived from propylene and ethylene, i.e., the propylene-alpha-olefin copolymer does not contain any other comonomer in an amount typically present as impurities in the ethylene and/or propylene feedstreams used during polymerization or an amount that would materially affect the heat of fusion, melting point, crystallinity, or melt flow rate of the propylene-alpha-olefin copolymer, or any other comonomer intentionally added to the polymerization process.

The propylene-alpha-olefin copolymer may have a triad tacticity of three propylene units, as measured by $^{13}$C NMR, of at least about 75%, at least about 80%, at least about 82%, at least about 85%, or at least about 90%. Preferably, the propylene-alpha-olefin copolymer has a triad tacticity of about 50 to about 99%, about 60 to about 99%, more preferably about 75 to about 99% or about 80 to about 99%. In some embodiments, the propylene-alpha-olefin copolymer may have a triad tacticity of about 60 to 97%.

The propylene-alpha-olefin copolymer has a heat of fusion ("$H_f$"), as determined by the Differential Scanning calorimetry ("DSC"), of about 75 J/g or less, preferably about 70 J/g or less, about 50 J/g or less, or about 35 J/g or less. The propylene-alpha-olefin copolymer may have a lower limit $H_f$ of about 0.5 J/g, about 1 J/g, or about 5 J/g. For example, the $H_f$ value may be anywhere from 1.0, 1.5, 3.0, 4.0, 6.0, or 7.0 J/g, to 30, 35, 40, 50, 60, 70, or 75 J/g.

The propylene-alpha-olefin copolymer may have a percent crystallinity, as determined according to the DSC procedure described herein, of about 2% to about 65%, preferably about 0.5 to about 40%, preferably about 1 to about 30%, and more preferably about 5 to about 35%, of isotactic polypropylene. The thermal energy for the highest order of propylene (i.e., 100% crystallinity) is estimated at 189 J/g. In some embodiments, the copolymer has a crystallinity less than 40%, in the range of about 0.25 to about 25%, or about 0.5 to about 22% of isotactic polypropylene. Embodiments of the propylene-alpha-olefin copolymer may have a tacticity index m/r from a lower limit of about 4 or about 6 to an upper limit of about 8 or about 10 or about 12. In some embodiments, the propylene-alpha-olefin copolymer has an isotacticity index greater than 0%, or within the range having an upper limit of about 50% or about 25%, and a lower limit of about 3% or about 10%.

In some embodiments, crystallinity of the propylene-alpha-olefin copolymer is reduced by copolymerization of propylene with limited amounts of one or more comonomers selected from: ethylene, $C_{4-20}$ alpha-olefins, and polyenes. In these copolymers, the amount of propylene-derived units present in the propylene-alpha-olefin copolymer ranges from an upper limit of about 99.9%, about 97%, about 95%, about 94%, about 92%, about 90%, or about 85%, to a lower limit of about 60%, about 68%, about 70%, about 71%, about 75%, about 76%, or about 80%, based on the total weight of the propylene-alpha-olefin copolymer.

The optional polyene may be any hydrocarbon structure having at least two unsaturated bonds wherein at least one of the unsaturated bonds is readily incorporated into a polymer. For example, the optional polyene may be selected from straight chain acyclic olefins, such as 1,4-hexadiene and 1,6-octadiene; branched chain acyclic olefins, such as 5-methyl-1,4-hexadiene, 3,7-dimethyl-1,6-octadiene, and 3,7-dimethyl-1,7-octadiene; single ring alicyclic olefins, such as 1,4-cyclohexadiene, 1,5-cyclooctadiene, and 1,7-cyclododecadiene; multi-ring alicyclic fused and bridged ring olefins, such as tetrahydroindene, norbornadiene, methyl-tetrahydroindene, dicyclopentadiene, bicyclo-(2.2.1)-hepta-2,5-diene, norbornadiene, alkenyl norbornenes, alkylidene norbornenes, e.g., ethylidene norbornene ("ENB"), cycloalkenyl norbornenes, and cycloalkyliene norbornenes (such as 5-methylene-2-norbornene, 5-ethylidene-2-norbornene, 5-propenyl-2-norbornene, 5-isopropylidene-2-norbornene, 5-(4-cyclopentenyl)-2-norbornene, 5-cyclohexylidene-2-norbornene, 5-vinyl-2-norbornene); and cycloalkenyl-substituted alkenes, such as vinyl cyclohexene, allyl cyclohexene, vinyl cyclooctene, 4-vinyl cyclohexene, allyl cyclodecene, vinyl cyclododecene, and tetracyclo(A-11,12)-5,8-dodecene. The amount of optional polyene-derived units present in the propylene-alpha-olefin copolymer ranges from an upper limit of about 15%, about 10%, about 7%, about 5%, about 4.5%, about 3%, about 2.5%, or about 1.5%, to a lower limit of about 0%, about 0.1%, about 0.2%, about 0.3%, about 0.5%, or about 1%, based on the total weight of the propylene-alpha-olefin copolymer. In a preferred embodiment, the propylene-alpha-olefin copolymer comprises diene-derived units (as used herein, "diene"). In some embodiments, the diene is present in an amount of about 10% or less, preferably about 5% or less, and more preferably about 3% or less by weight of the propylene-alpha-olefin copolymer. In some embodiments, the diene is present in an amount of about 0.1 to about 6%, about 0.1 to about 5%, preferably about 0.1 to about 4%, more preferably about 0.1 to about 2%, and most preferably about 0.1 to about 1% by weight of the propylene-alpha-olefin copolymer.

The propylene-alpha-olefin copolymer may have a single peak melting transition as determined by DSC. In one embodiment, the copolymer has a primary peak transition of about 90° C. or less, with a broad end-of-melt transition of about 110° C. or greater. The peak "melting point" ("Tm") is defined as the temperature of the greatest heat absorption within the range of melting of the sample. However, the copolymer may show secondary melting peaks adjacent to the principal peak, and/or at the end-of-melt transition. For the purposes of this disclosure, such secondary melting peaks are considered together as a single melting point, with the highest of these peaks being considered the Tm of the propylene-alpha-olefin copolymer. The propylene-alpha-olefin copolymer may have a Tm of about 100° C. or less, about 90° C. or less, about 80° C. or less, or about 70° C. or less. In one embodiment, the propylene-alpha-olefin copolymer has a Tm of about 25 to about 100° C., preferably about 25 to about 85° C., about 25 to about 75° C., or about 25 to about 65° C. In some embodiments, the propylene-alpha-olefin copolymer has a Tm of about 30 to about 80° C., preferably about 30 to 70° C.

The propylene-alpha-olefin copolymer may have a density of about 0.850 to about 0.920 g/cm$^3$, about 0.860 to about 0.900 g/cm$^3$, preferably about 0.860 to about 0.890 g/cm$^3$, at room temperature as measured per ASTM D-1505.

The propylene-alpha-olefin copolymer may have a melt flow rate ("MFR"), as measured per ASTM D1238, 2.16 kg at 230° C., of at least about 0.2 dg/min. In one embodiment, the propylene-alpha-olefin copolymer MFR about 0.5 to about 5000 dg/min, about 1 to about 2500 dg/min, about 1.5 to about 1500 dg/min, about 2 to about 1000 dg/min, about 5 to about 500 dg/min, about 10 to about 250 dg/min, about 10 to about 100 dg/min, about 2 to about 40 dg/min, or about 2 to about 30 dg/min. In some preferred embodiments, the propylene-alpha-olefin copolymer MFR is about 0.5 to about 50 dg/min, about 1 to about 30 dg/min, or about 2 to about 10 dg/min.

The propylene-alpha-olefin copolymer may have an Elongation at Break of less than about 2000%, less than about 1000%, or less than about 800%, as measured per ASTM D412.

The propylene-alpha-olefin copolymer may have a weight average molecular weight (Mw) of about 5,000 to about 5,000,000 g/mole, preferably about 10,000 to about 1,000,000 g/mole, and more preferably about 50,000 to about 400,000 g/mole; a number average molecular weight (Mn) of about 2,500 to about 2,500,00 g/mole, preferably about 10,000 to about 250,000 g/mole, and more preferably about 25,000 to about 200,000 g/mole; and/or a z-average molecular weight (Mz) of about 10,000 to about 7,000,000 g/mole, preferably about 80,000 to about 700,000 g/mole, and more preferably about 100,000 to about 500,000 g/mole. The propylene-alpha-olefin copolymer may have a molecular weight distribution ("MWD") of about 1.5 to about 20, or about 1.5 to about 15, preferably about 1.5 to about 5, and more preferably about 1.8 to about 5, and most preferably about 1.8 to about 3 or about 4.

Preferred propylene-alpha-olefin copolymers are available commercially under the trade names VISTAMAXX™ (ExxonMobil Chemical Company, Houston, Tex., USA), VERSIFY™ (The Dow Chemical Company, Midland, Mich., USA), certain grades of TAFMER™ XM or NOTIO™ (Mitsui Company, Japan), and certain grades of SOFTEL™ (Basell Polyolefins of the Netherlands). The particular grade(s) of commercially available propylene-alpha-olefin copolymer suitable for use in the invention can be readily determined using methods commonly known in the art.

The composition of the invention, e.g., a masterbatch, may include one or more different propylene-alpha-olefin copolymers, i.e., propylene-alpha-olefin copolymers each having one or more different properties such as, for example, different comonomer or comonomer content. Such combinations of various propylene-alpha-olefin copolymers are all within the scope of the invention.

In one embodiment, the propylene-alpha-olefin copolymer is an elastomer including propylene-derived units, diene-derived units, and ethylene-derived units, and having isotactic polypropylene crystallinity, a melting point by DSC equal to or less than 110° C., and a heat of fusion of from about 5 J/g to about 50 J/g. The propylene-derived units are present in an amount of about 80 to about 90%, based on the combined weight of units derived from propylene, diene, and ethylene. The diene-derived units are present in an amount of about 0.3 to about 3%, based on the combined weight of units derived from propylene, diene, and ethylene. The ethylene-derived units are present in an amount of about 10 to about 20%, based on the combined weight of units derived from propylene, diene, and ethylene.

Embodiments of the invention include a semicrystalline propylene-based polymer having isotactic polypropylene crystallinity and optionally including a diene. Embodiments of the invention also include crosslinkable and crosslinked, semicrystalline, propylene-based polymers and blends including such polymers.

In one embodiment, elastomeric properties of the propylene-alpha-olefin copolymer are improved by curing the propylene-alpha-olefin copolymer to various degrees. In another embodiment, the propylene-alpha-olefin copolymer is cured to various degrees to permit convenient processing. In some embodiments, the propylene-alpha-olefin copolymer includes a diene to facilitate curing and optimal end use performance in various options of formulation and processing. In other embodiments, such as when using radiation to induce the crosslinking reaction, the presence of diene in the propylene-alpha-olefin copolymer is optional. Crosslinked propylene-alpha-olefin copolymers, their properties and method of manufacturing are described in, for example U.S. Publication No. 2005/107530, the contents of which are incorporated herein by reference.

In various embodiments, the propylene-alpha-olefin copolymer is an elastomer having some or all of the following characteristics, in any combination, where ranges from any recited upper limit to any recited lower limit are contemplated:
(a) the diene is 5-ethylidene-2-norbornene or 5-vinyl-2-norbornene;
(b) the diene-derived units are present in an amount of about 1 to about 3%, or about 0.5 to about 1.5%, based on the combined weight of units derived from propylene, diene, and ethylene; and
(c) the elastomer has a Mooney viscosity ML(1+4) at 125° C. of from 0.5 to 100, or from 5 to 40.

In another embodiment, the propylene-alpha-olefin copolymer is a crosslinked elastomer comprising (a) propylene-derived units and (b) at least 0.1% of units derived from one or more additional components selected from the group consisting of ethylene, $C_4$-$C_{20}$ alpha-olefins, and diene, based on the total weight of components (a) and (b). The crosslinked elastomer has isotactic polypropylene crystallinity, a melting point by DSC equal to or less than about 110° C., and a heat of fusion of about 5 J/g to about 50 J/g. The crosslinked elastomer is crosslinked to a degree so as to provide at least about 2%, at least about 10%, at least about 20%, or about 2% to about 95% by weight, crosslinked insolubles, or it is crosslinked to a degree so as to provide the elastomer with a viscosity ratio of from about 1 or about 1.2 to about 10.

In various embodiments, features of the crosslinked elastomer include some or all of the following characteristics, in any combination, where ranges from any recited upper limit to any recited lower limit are contemplated:
(a) the propylene-derived units are present in an amount of at least about 80%, based on the total weight of components (a) and (b);
(b) the elastomer has a tension set after 200% elongation of less than about 50% and an ultimate tensile strength of at least about 1000 psi (6.89 MPa);
(c) component (b) of the crosslinked elastomer comprises diene-derived units in an amount of about 0.1 to about 5%, or about 0.5 to about 1.5%, or about 1 to about 3%, based on the total weight of components (a) and (b); and
(d) component (b) of the crosslinked elastomer comprises units derived from 5-s vinyl-2-norbornene or 5-ethylidene-2-norbornene.

The propylene-alpha-olefin copolymer may comprise copolymers prepared according to the procedures described in WO 02/36651, U.S. Pat. No. 6,992,158, and/or WO 00/01745, the contents of which are incorporated herein by reference. Preferred methods for producing the propylene-alpha-olefin copolymer may be found in U.S. Pat. Nos. 7,232,871 and 6,881,800, the contents of which are incorporated herein by reference.

The invention is not limited by any particular polymerization method for preparing the propylene-alpha-olefin copolymer, and the polymerization processes described herein are not limited by any particular type of reaction vessel.

The propylene-alpha-olefin copolymer can be polymerized by a single stage, steady state polymerization conducted in a well-mixed continuous feed polymerization reactor. The polymerization can be conducted in solution, although other polymerization procedures, such as gas phase or slurry polymerization, are also contemplated. The process can be described as a continuous, non-batch process that, in its steady state operation, is exemplified by removal of amounts of polymer made per unit time, being substantially equal to the amount of polymer withdrawn from the reaction vessel per unit time. As used herein, "substantially equal" means that these amounts, polymer made per unit time, and polymer withdrawn per unit time, are in ratios of one to other, of from about 0.9:1; about 0.95:1; about 0.97:1; or about 1:1. The polymerization is accomplished in a single step or in a single reactor, although multiple reactors may also be used.

In one embodiment, the propylene-alpha-olefin copolymer is prepared by a process which includes the following steps: a) feeding solvent and monomers, including propylene and optionally one or more of ethylene, $C_{4-20}$ alpha-olefins, and non-conjugated diene, in predetermined proportions to a polymerization reactor, b) adding a soluble catalyst to the reactor, and c) polymerizing the monomers in solution to produce an effluent containing a polymer. In order to remove polar compounds that act as catalyst poisons, the solvent and monomer feeds can be purified over mole sieves, alumina beds, or other absorbents as known in the art. The reactor temperature can be controlled by methods well known in the art such as autorefrigeration, prechilled feeds (adiabatic reactors), cooling coils, and combinations of these techniques. The pressure should be sufficient to keep the reactor contents in solution at the reactor temperature. Polymerization is carried out at temperatures in the range of from about −20° C. to about 200° C. The residence time per reactor is maintained at from 1 to 180 minutes. The polymer concentration in the effluent of the reactors is maintained in the range of about 1 to about 20% by weight. The overall polymerization rate is set by the catalyst and monomer feed rates. Polymer composition is controlled by adjusting the monomer feed rate to a reactor. Polymer molecular weight is set by choosing the reactor temperature, monomer concentration, and by optionally adding chain transfer agents, such as hydrogen. The polymer product can be conventionally recovered from the effluent by coagulation with a nonsolvent such as isopropyl alcohol, acetone, or n-butyl alcohol, or the polymer can be recovered by stripping the solvent or other media with heat or steam. One or more conventional additives such as antioxidants can be incorporated in the polymer during the recovery procedure.

In one embodiment, a catalyst system used to produce the propylene-alpha-olefin copolymer and includes one or more transition metal compounds and one or more activators. When alumoxane or aluminum alkyl activators are used, the combined pre-catalyst-to-activator molar ratio is from about 1:5000 to about 10:1. When ionizing activators are used, the combined pre-catalyst-to-activator molar ratio is from about 10:1 to about 1:10. Multiple activators may be used, including using mixtures of alumoxanes or aluminum alkyls with ionizing activators.

In another embodiment, the catalyst system includes a bis(cyclopentadienyl) metal compound and either (1) a non-coordinating compatible anion activator, or (2) an alumoxane activator. Non-limiting examples of catalyst systems which can be used are described in U.S. Pat. Nos. 5,198,401 and 5,391,629, the contents of which are incorporated herein by reference.

In another embodiment, the propylene-alpha-olefin copolymer is made in the presence of an activating cocatalyst which is a precursor ionic compound comprising a halogenated tetra-aryl-substituted Group 13 anion wherein each aryl substituent contains at least two cyclic aromatic rings. In a particular aspect of this embodiment, the propylene-alpha-olefin copolymer contains greater than about 0.2 parts per million, greater than about 0.5 parts per million, greater than about 1 part per million, or greater than about 5 parts per million of the residues of the activating cocatalyst.

In another embodiment, the propylene-alpha-olefin copolymer is produced using a single-sited polymerization catalyst, which allows only a single statistical mode of addition of the first and second monomer sequences. In a particular aspect of this embodiment, the reactor is a continuous flow stirred tank polymerization reactor which allows only a single polymerization environment for substantially all of the polymer chains of the polymer.

One or more reactors in series or in parallel may be used in the present invention. The catalyst component and activator may be delivered as a solution or slurry, either separately to the reactor, activated in-line just prior to the reactor, or pre-activated and pumped as an activated solution or slurry to the reactor. Polymerizations are carried out in either single reactor operation, in which monomer, comonomers, catalyst/activator, scavenger, and optional modifiers are added continuously to a single reactor or in series reactor operation, in which the above components are added to each of two or more reactors connected in series. The catalyst components can be added either to the first reactor in the series or to both reactors with one component being added to first reaction and another component to the other reactors.

For further general process condition information, see U.S. Pat. No. 5,001,205, and PCT publications WO 96/33227 and WO 97/22639, the contents of which are incorporated herein by reference. For further information on gas phase polymerization processes, see U.S. Pat. Nos. 4,543,399, 4,588,790, 5,028,670, 5,317,036, 5,352,749, 5,405,922, 5,436,304, 5,453,471, 5,462,999, 5,616,661, 5,627,242, 5,665,818, 5,668,228, and 5,677,375, and European publications EP-A-0 794 200, EP-A-0 802 202 and EP-B-634 421, the contents of which are incorporated herein by reference. For information on how to introduce a liquid catalyst system into a fluidized bed polymerization into a particle lean zone, see U.S. Pat. No. 5,693,727, the contents of which are incorporated herein by reference. For further information on slurry polymerization processes, see U.S. Pat. Nos. 3,248,179 and 4,613,484, the contents of which are incorporated herein by reference. PCT publication WO 96/08520 and U.S. Pat. No. 5,712,352, the contents of which are incorporated herein by reference, describe a polymerization process which is operated in the absence of or essentially free of any scavengers, although the use of scavengers is contemplated.

Pesticide

The compositions of the invention comprise a pesticide, for example, an insecticide, miticide, acaricide, nematocide, ovicide, or larvicide. Known pesticides include organochlorine compounds such as aldrin, chlordane, chlordecone, dieldrin, endosulfan, endrin, heptachlor, hexachlorobenzene, lindane (gamma-hexachlorocyclohexane), methoxychlor, mirex, pentachlorophenol, TDE, and dichlorodiphenyltrichloroethane (DDT); organophosphates such as acephate, azinphos-methyl, bensulide, chlorethoxyfos, chlorpyrifos, chlorpyriphos-methyl, diazinon, dichlorvos (DDVP), dicrotophos, dimethoate, disulfoton, ethoprop, fenamiphos, fenitrothion, fenthion, fosthiazate, malathion, methamidophos, methidathion, mevinphos, naled, omethoate, oxydemeton-methyl, parathion, parathion-methyl, phorate, phosalone, phosmet, phostebupirim, phoxim, pirimiphos-methyl, profenofos, terbufos, tetrachlorvinphos, tribufos, trichlorfon; carbamates such as aldicarb, carbofuran, furadan, fenoxycarb, carbaryl, ethienocarb, fenobucarb, and 2-(1-methylpropyl)phenyl methylcarbamate; neonicotinoids such as acetamiprid, clothianidin, imidacloprid, nitenpyram, nithiazine, thiacloprid, thiamethoxam; and pyrethroids such as allethrin, bifenthrin, beta-cyfluthrin, cypermethrin, cyphenothrin, deltamethrin, esfenvalerate, etofenprox, fenpropathrin, fenvalerate, flucythrinate, imiprothrin, lambda-cyhalothrin, metofluthrin, permethrin, prallethrin, resmethrin, silafluofen, sumithrin, tau-fluvalinate, tefluthrin, tetramethrin, tralomethrin, and transfluthrin.

In a preferred embodiment, the pesticide is a pyrethroid. Preferred pyrethroids are compounds of formula I:

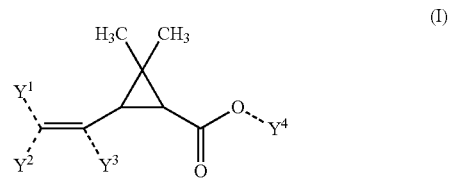

wherein $Y^1$, $Y^2$, and $Y^3$ may be the same or different and are hydrogen, a halogen, or a $C_{1-40}$ hydrocarbon radical optionally containing at least one heteroatom belonging to the Groups 13-17 of the Periodic Table of Elements; and $Y^4$ is a $C_{1-40}$ hydrocarbon radical optionally containing at least one heteroatom belonging to the Groups 13-17 of the Periodic Table of Elements.

In a preferred embodiment, the pyrethroid is (a) an allethrin, cinerin, jasmolin, or pyrethrin compound, or (b) a compound of formula II:

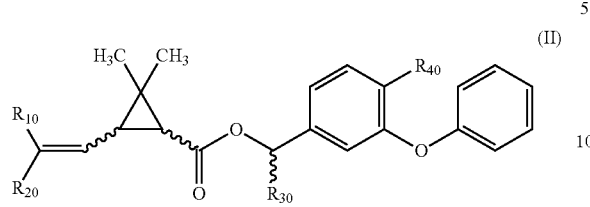

wherein $R^{10}$ and $R^{20}$ may be the same or different and are H, CH, OCH, SCH, CF, OCF, F, Cl or Br;
$R^{30}$ is H, CH, CN, CF, F, Cl or BR;
$R^{40}$ is H, CH, CF, OH, SH, F, Cl or Br; and
the symbol ⁓ represents a bond having R or S configuration.

Preferably, the pyrethroid comprises at least one of allethrin, bifenthrin, bioresmethrin, cyclethrin, cyhalothrin, cyfluthrin, cypermethrin, cyphenothrin, deltamethrin, fenpropathrin, flumethrin, or permethrin. More preferably, the pyrethroid comprises at least one of deltamethrin, cypermethrin (preferably α-cypermethrin), cyhalothrin (preferably λ-cyhalothrin), or allethrin I.

Preferably, the compositions of the invention comprise a pyrethroid that is a condensation adduct of formula T1-T2 (the "T1-T2 adduct"), wherein T1 comprises at least one pyrethroid substantially stable up to a temperature of at least about 150° C., and T2 comprises an ethylenically unsaturated substance selected from at least one of a surfactant or vinyl phosphate.

The T1-T2 adduct can be prepared by methods described in WO 2004/089086 and WO2008/141928, the contents of which are incorporated herein by reference. The T1-T2 adduct may be formed by contacting T1 and T2 at a temperature of at least about 80° C., preferably from about 80 to about 150° C.

In a preferred embodiment, the T1-T2 adduct has a solubility in ethanol at room temperature of at least about 75 wt. %, more preferably about 75 to about 90 wt. %. Preferably, the T1-T2 adduct comprises about 75 to about 96% of T1 and about 25% to about 4% by weight of T2, by weight of the adduct.

The T1-T2 adduct is preferably present in an amount of about 0.01 to about 40%, more preferably about 0.05 to about 40%, about 0.1 to about 30%, about 1 to about 30%, about 5 to about 30%, or about 20 to about 30% by weight of the composition.

T1 comprises at least one pyrethroid that is substantially stable, i.e., at least a pesticidally effective amount of the pyrethroid is retained, up to a temperature of at least about 150° C., preferably up to at least about 300° C. In this respect, preferred pyrethroids include allethrin I, which is stable up to a temperature of more than 400° C. (see, e.g., The Merck Index, 12th ed., 1996, p. 255), deltamethrin, which is stable up to 320° C., and cypermethrin, which has a flash point of more than 300° C.

T2 comprises an ethylenically unsaturated substance selected from at least one of a surfactant or vinyl phosphate. Preferably, T2 is substantially stable at a temperature of at least about 150° C., more preferably up to about 300° C. In one embodiment, T2 is a surfactant comprising an amine or polyamine of formula III or IV:

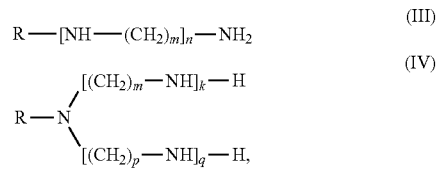

a polyoxyalkylenated amine or polyamine of formula V:

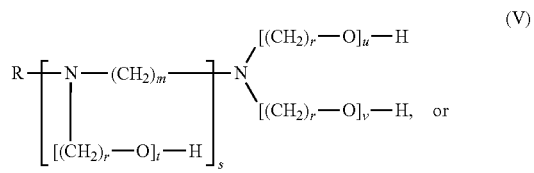

a polyoxyalkylenated alkenylphenol of formula VI:

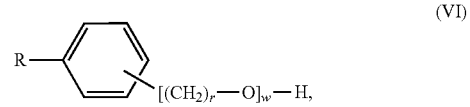

wherein R is a $C_{8-22}$ unsaturated aliphatic hydrocarbon radical having a linear or branched chain, preferably a linear chain; k is an integer from 1 to 8; m is an integer from 2 to 8; n is an integer from 0 to 8; p is an integer from 1 to 8; q is an integer from 1 to 8; r is an integer from 2 or 3; s is an integer from 0 to 8; t is an integer from 1 to 8; u is an integer from 0 to 8; v is an integer from 0 to 8; and w is an integer from 3 to 8.

In one embodiment, T2 is a vinyl phosphate having the structure VII:

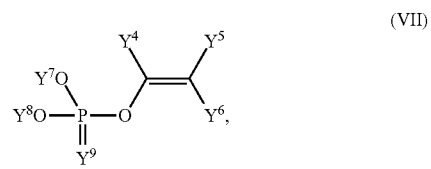

wherein $Y^7$ and $Y^8$ may be the same or different and are a $C_{1-4}$ alkyl group; $Y^9$ is oxygen or sulphur; $Y^4$, $Y^5$ and $Y^6$ may be the same or different and are hydrogen, a halogen, or a $C_{1-40}$ hydrocarbon radical optionally containing at least one heteroatom belonging to the Groups 13-17 of the Periodic Table; no more than two of $Y^4$, $Y^5$ and $Y^6$ are hydrogen; and two of $Y^4$, $Y^5$ and $Y^6$ may be joined to form a heterocyclic ring containing nitrogen, oxygen or sulphur.

Preferably, the vinyl phosphate is at least one of dichlorvos, pirimiphos-methyl, chlorpyrifos, chlorfenvinphos, or crotoxyphos.

Slip Agents

The compositions of the invention may further comprise a slip agent. Propylene-alpha-olefin copolymers, particularly propylene-ethylene copolymers, can be tackier than conventional fibers made from polyolefins such as polyethylene and polypropylene. Thus, slip agents are useful in polyolefin-based polymers to limit filament and fiber tackiness. As used herein, a "slip agent" is one or more compounds added to a polyolefin composition to facilitate removal of the polymer from, for example, a mold or other surface.

The slip agent may be added to the composition in neat form, diluted, and/or as a masterbatch in, for example, polyolefin polymers such as polypropylene, polystyrene, low density polyethylene, high density polyethylene, or propylene-alpha-olefin copolymers.

In one embodiment, the composition is a layer comprising one or more slip agents, preferably in a total amount of about 0.01 to about 20% by weight of the layer in which contains the slip agent. Preferably, the total amount of slip agent is about 0.05 to about 20%, about 0.05 to about 10%, about 0.10 to about 5%, about 0.15 to about 4%, or about 0.50 to about 3% by weight of the layer in which contains the slip agent. Suitable ranges may include any upper limit with any lower limit disclosed herein.

In another embodiment, the composition is a fiber comprising one or more slip agents, preferably in a total amount of at least about 500 ppm, at least about 1000 ppm, or at least about 1500 ppm, more preferably at least about 2000 ppm, at least about 2500 ppm, at least about 3000 ppm, at least about 5000 ppm, at least about 7500 ppm, at least about 10,000 ppm, or at least about 15,000 ppm of slip agent.

In one embodiment, the slip agent is an organic amine compound, i.e., contains an amine group bound to a hydrocarbon group. In one embodiment, the slip agent is a fatty acid amine or a fatty acid amide. In some embodiments, the slip agent may have one or more paraffinic or olefinic groups bound to a nitrogen atom, forming an amine or an amide compound. The paraffinic or olefinic group may be, for example, a polar or ionic moiety as a side chain or within the amine/amide backbone. Such polar or ionic moieties can include hydroxyl groups, carboxylate groups, ether groups, ester groups, sulfonate groups, sulfite groups, nitrate groups, nitrite groups, phosphate groups, phosphate groups, and combinations thereof.

In one embodiment, the slip agent is an alkyl-ether amine having the formula $(R'OH)_{3-x}NR_x$, wherein R is selected from the group consisting of hydrogen, $C_{1-40}$ alkyl radicals, $C_{2-40}$ alkylethers, $C_{1-40}$ alkylcarboxylic acids, and $C_{2-40}$ alkylesters; R' is selected from the group consisting of $C_{1-40}$ alkyl radicals, $C_2$-40 alkylethers, $C_{1-40}$ carboxylic acids, and $C_{2-40}$ alkylesters; and x is 0, 1, 2 or 3, preferably 0 or 1, more preferably 1. In one embodiment, R is selected from the group consisting of hydrogen and $C_{5-40}$ alkyl radicals; and R' is selected from the group consisting of $C_{5-40}$ alkyl radicals and $C_{5-40}$ alkylethers.

In another embodiment, the slip agent is an amide-containing compound having the formula: $RCONH_2$, wherein R is a $C_{5-23}$ alkyl or alkene. In another embodiment, the slip agent is a fatty acid amide having the formula: $(R'CO)_{3-x}NR''_x$, wherein R'' is selected from the group consisting of hydrogen, $C_{10-60}$ alkyl radicals and $C_{10-60}$ alkene radicals and substituted versions thereof; R' is selected from the group consisting of $C_{10-60}$ alkyl radicals, $C_{10-60}$ alkene radicals, and substituted versions thereof; and x is 0, 1, 2 or 3, preferably 1 or 2, more preferably 2. As used herein, an "alkene" radical is a radical having one or more double-bond unsaturation in the radical chain (e.g., $—CH_2CH_2CH_2CH_2CH=CHCH_2CH_2CH_2CH_2CH_2CH_3$), and "substituted" means substitution anywhere along the hydrocarbon chain of a hydroxyl group, carboxyl group, halide, or sulfate group.

In some embodiments, the slip agent contains an unsaturated amide. In one embodiment, the unsaturated amide-containing slip agent has the formula: $RCONH_2$, wherein R is a $C_{5-23}$ alkene. In another embodiment, the unsaturated amide-containing slip agent has the formula: $(R'CO)_{3-x}NR''_x$, wherein R'' is selected from the group consisting of hydrogen, $C_{10-60}$ alkyl radicals and $C_{10-60}$ alkene radicals and substituted versions thereof; R' is selected from the group consisting of $C_{10-60}$ alkene radicals and substituted versions thereof; and x is 0, 1, 2 or 3, preferably 1 or 2, more preferably 2. In some embodiments, the unsaturated amide-containing slip agent is at least one of palmitoleamide, oleamide, linoleamide, or erucamide. In other embodiments, the unsaturated amide-containing slip agent is at least one of oleamide or erucamide.

In other embodiments, the slip agent contains a saturated amide. In one embodiment, the saturated amide-containing slip agent has the formula: $RCONH_2$, wherein R is a $C_{5-23}$ alkyl. In another embodiment, the saturated amide-containing slip agent has the formula: $(R'CO)_{3-x}NR''_x$, wherein R'' is selected from the group consisting of hydrogen, $C_{10-60}$ alkyl radicals and $C_{10-60}$ alkene radicals and substituted versions thereof; R' is selected from the group consisting of $C_{10-60}$ alkyl radicals and substituted versions thereof; and x is 0, 1, 2 or 3, preferably 1 or 2, more preferably 2. In some embodiments, the saturated amide-containing slip agent is at least one of lauramide, myristamide, palmitamide, stearamide, or behenamide. In other embodiments, the saturated amide-containing slip agent is at least one of stearamide or behenamide.

Non-limiting examples of slip agents include bis(2-hydroxyethyl) isodecyloxypropylamine, poly(5)oxyethylene isodecyloxypropylamine, bis(2-hydroxyethyl) isotridecyloxypropylamine, poly(5)oxyethylene isotridecyloxypropylamine, bis(2-hydroxyethyl) linear alkyloxypropylamine, bis(2-hydroxyethyl) soya amine, poly(15)oxyethylene soya amine, bis(2-hydroxyethyl) octadecylamine, poly(5)oxyethylene octadecylamine, poly(8)oxyethylene octadecylamine, poly(10)oxyethylene octadecylamine, poly(15)oxyethylene octadecylamine, bis(2-hydroxyethyl) octadecyloxypropylamine, bis(2-hydroxyethyl) tallow amine, poly(5)oxyethylene tallow amine, poly(15)oxyethylene tallow amine, poly(3) oxyethylene-1,3-diaminopropane, bis(2-hydroxyethyl) cocoamine, bis(2-hydroxyethyl)isodecyloxypropylamine, poly(5)oxyethylene isodecyloxypropylamine, bis(2-hydroxyethyl) isotridecyloxypropylamine, poly(5)oxyethylene isotridecyloxypropylamine, bis(2-hydroxyethyl) linear alkyloxypropylamine, bis(2-hydroxyethyl) soya amine, poly(15) oxyethylene soya amine, bis(2-hydroxyethyl) octadecylamine, poly(5)oxyethylene octadecylamine, poly(8) oxyethylene octadecylamine, poly(10)oxyethylene octadecylamine, poly(15)oxyethylene octadecylamine, bis (2-hydroxyethyl) octadecyloxypropylamine, bis(2-hydroxyethyl) tallow amine, poly(5)oxyethylene tallow amine, poly (15)oxyethylene tallow amine, poly(3) oxyethylene-1,3-diaminopropane, bis(2-hydroxethyl) cocoamine, valeramide, caproicamide, erucamide, caprylicamide, pelargonicamide, capricamide, lauricamide, lauramide, myristicamide, myristamide, palmiticamide, palmitoleamide, palmitamide, margaric (daturic) amide, stearicamide, arachidicamide, behenicamide, behenamide, lignocericamide, linoleamide, ceroticamide, carbocericamide, montanicamide, melissicamide, lacceroicamide, ceromelissic (psyllic) amide, geddicamide, 9-octadecenamide, oleamide, stearamide, tallow bis(2-hydroxyethyl)amine. cocobis(2-hydroxyethyl)amine, octadecylbis(2-hydroxyethyl)amine, oleylbis(2-hydroxyethyl)amine, ceroplastic amide, and combinations thereof. Commercial examples of useful slip agents include ATMER™ compounds (Ciba Specialty Chemicals), ARMID™, ARMOFILM™ and ARMOSLIP™ compounds and NOURYMIX™ concentrates (Akzo Nobel Chemicals), and CROTAMID™ compounds (Croda Universal Inc).

Compositions of the invention may include one or more different slip agents. For example, in one embodiment a composition may comprise one or more unsaturated amide-containing slip agents, and in another embodiment one or more unsaturated amide-containing slip agents and one or more saturated amide-containing slip agents. In some embodiments, a composition includes a combination of low molecular weight (Mw) and thus faster migrating amides, e.g., erucamide or oleamide, and higher molecular weight (Mw) and thus slower migrating amides, e.g., behenamide or stearamide.

In one embodiment, the composition is a masterbatch comprising the propylene-alpha-olefin copolymer, the condensation adduct of formula T1-T2, and one or more modifiers. A first modifier is an unsaturated amide-containing slip agent. A second modifier is at least one of (a) a second unsaturated amide-containing slip agent, which may be the same or different than the first unsaturated amide-containing slip agent; (b) a saturated amide-containing slip agent; or (c) an anti-blocking agent. In one embodiment, the second modifier consists essentially of the second unsaturated amide-containing slip agent and the saturated amide-containing slip agent. In another embodiment, the second modifier consists essentially of the saturated amide-containing slip agent.

Anti-Blocking Agents

The compositions of the invention may further comprise an anti-blocking agent. Anti-blocking agents are useful in polyolefin-based polymers to limit filament and fiber tackiness. As used herein, an "anti-blocking" agent is one or more compounds, including without limitation minerals or treated minerals, added to a polyolefin to reduce the tackiness of the polyolefin, especially when used in polyolefin fibers.

The anti-blocking agent may be added to the composition in neat form, diluted; and/or as a masterbatch in, for example, polyolefinic polymers such as polypropylene, polystyrene, low density polyethylene, or high density polyethylene, or propylene-alpha-olefin copolymers.

In some embodiments, the anti-blocking agent includes a porous inorganic oxide material, such as metal oxides of Group 2, 3, 4, 5, 13, or 14 from the Periodic Table of Elements. Preferred metal oxides contain elements from Groups 4, 13, and 14. Non-limiting examples of suitable anti-blocking agents include silica, alumina, silica-alumina, magnesia, titania, zirconia, diatomaceous earth, and mixtures thereof. A commercially available suitable anti-blocking agent is Sibelite™ M4000 (Sibelco), a high purity silica.

Compositions of the invention may include one or more different anti-blocking agents. In one embodiment, the composition comprises an anti-blocking agent in an amount (if more than one anti-blocking agent is present, a total amount) of about 0.05 to about 20%, about 1 to about 15%, about 1.5 to about 10%, about 2.5 to about 6.5%, or about 2 to about 8% by weight of the composition. Suitable ranges may include any upper limit with any lower limit disclosed herein. In some embodiments, the composition comprises at least about 1%, at least about 1.5%, at least about 2%, at least about 3%, or at least about 5% of anti-blocking agent by weight of the composition.

In some embodiments, the composition is substantially free of anti-blocking agent. As used herein, "substantially free of anti-blocking agent" means an anti-blocking agent is not intentionally added to the composition, or is present in an amount of less than about 3% by weight of the composition. In these embodiments, the anti-blocking agent is preferably in an amount of less than about 1%, more preferably less than about 0.5%, and even more preferably less than about 0.1% by weight of the composition.

In some embodiments, the composition is substantially free of talc, i.e., talc is not intentionally added to the composition, or is present in an amount of less than about 3% by weight of the composition. In these embodiments, talc is preferably in an amount of less than about 1%, more preferably less than about 0.5%, and even more preferably less than about 0.1% by weight of the composition.

Test Methods

Molecular weight (Mn, Mw, and Mz) and MWD is determined as follows and as described in Verstate et al., 21 MACROMOLECULES 3360 (1988). Conditions described herein govern over published test conditions. Molecular weight and MWD are measured using a Waters 150 gel permeation chromatograph equipped with a Chromatix KMX-6 on-line light scattering photometer. The system is used at 135° C. with 1,2,4-trichlorobenze as the mobile phase. Showdex (Showa-Denko America, Inc.) polystyrene gel columns 802, 803, 804, and 805 are used. This technique is discussed in Verstate et al., 21 MACROMOLECULES 3360 (1988). No corrections for column spreading are employed; however, data on generally acceptable standards, e.g., National Bureau of Standards Polyethylene 1484, and anionically produced hydrogenated polyisoprenes (an alternating ethylenepropylene copolymer) demonstrate that such corrections on Mw/Mn or Mz/Mw are less than 0.05 units. Mw/Mn was calculated from an elution time-molecular relationship whereas Mz/Mw was evaluated using the light scattering photometer. The numerical analysis can be performed using the commercially available computer software GPC2, MOLWT2 available from LDC/Milton Roy-Rivera Beach, Fla.

DSC is determined as follows. About 0.5 grams of polymer is weighed and pressed to a thickness of about 15 to 20 mils (about 381-508 microns) at about 140-150° C., using a "DSC mold" and MYLAR™ film as a backing sheet. The pressed polymer sample is allowed to cool to ambient temperatures by hanging in air (the MYLAR™ film backing sheet is not removed). The pressed polymer sample is then annealed at room temperature (about 23-25° C.) for about 8 days. At the end of this period, a 15-20 mg disc is removed from the pressed polymer sample using a punch die and is placed in a 10 microliter aluminum sample pan. The disc sample is then placed in a DSC (Perkin Elmer Pyris 1 Thermal Analysis System) and is cooled to about −100° C. The sample is heated at about 10° C./min to attain a final temperature of about 165° C. The thermal output, recorded as the area under the melting peak of the disc sample, is a measure of the heat of fusion and can be expressed in Joules per gram (J/g) of polymer and is automatically calculated by the Perkin Elmer system. Under theses conditions, the melting profile shows two (2) maxims, the maxima at the highest temperature is taken as the melting point within the range of melting of the disc sample relative to a baseline measurement for the increasing heat capacity of the polymer as a function of temperature.

Triad tacticity is determined as follows. The tacticity index, expressed herein as "m/r", is determined by $^{13}$C nuclear magnetic resonance ("NMR"). The tacticity index m/r is calculated as defined by H. N. Cheng in 17 MACROMOLECULES 1950 (1984), incorporated herein by reference. The designation "m" or "r" describes the stereochemistry of pairs of contiguous propylene groups, with "m" referring to meso and "r" referring to racemic. An m/r ratio of 1.0 generally describes a syndiotactic polymer, and an m/r ratio of 2.0 generally describes an atactic material. An isotactic material theoretically may have a m/r ratio approaching infinity, and many by-product atactic polymer have sufficient isotactic content to result in an m/r ratio of greater than 50.

Additional Polymer

The composition of the invention may further comprise one or more additional polymers, which may be at least one of a propylene homopolymer or propylene copolymer, commonly known as reactor copolymers or impact copolymers. In embodiments where the additional polymer includes a propylene copolymer, the propylene copolymer may be a graft copolymer, block copolymer, or random copolymer.

The amount of propylene-derived units present in the additional polymer component may be at least about 90%, at least about 92%, at least about 95%, at least about 97%, or about 100%, based on the total weight of the additional polymer.

In one embodiment, the additional polymer includes a random copolymer of propylene and at least one comonomer selected from at least one of ethylene and $C_{4-12}$ alpha-olefins. In a particular aspect of this embodiment, the amount of comonomer has an upper limit of about 9%, about 8%, or about 6%, and a lower limit of about 2%, based on the total weight of the additional polymer.

In one embodiment, the additional polymer includes a copolymer of ethylene, an alpha-olefin, and optionally a diene. The amount of ethylene-derived units in the copolymer may be 50 mol % or greater. In one embodiment, the copolymer is an ethylene-hexene copolymer. In another embodiment the copolymer is a copolymer of ethylene, propylene, and diene known as EPDM. In a particular aspect of this embodiment, the amount of propylene-derived units in the copolymer is 40 mol % or greater.

Other Additives

As will be evident to those skilled in the art, the compositions of the present invention may comprise other additives. Various additives may be present to enhance a specific property or may be present as a result of processing of the individual components. Additives which may be incorporated include, but are not limited to processing oils, fire retardants, antioxidants, plasticizers, dyes (e.g., blue or green dyes), pigments, vulcanizing or curative agents, vulcanizing or curative accelerators, cure retarders, processing aids, flame retardants, tackifying resins, flow improvers, and the like. Antiblocking agents such as the those described above, coloring agents, lubricants, mold release agents, nucleating agents, reinforcements, and fillers (including granular, fibrous, or powder-like) may also be used. Nucleating agents and fillers may improve the rigidity of the article. The list described herein is not intended to be inclusive of all types of additives which may be employed with the present invention. Those of skill in the art will appreciate that other additives may be employed to enhance properties of the composition. As is understood by those skilled in the art, the compositions of the present invention may be modified to adjust the characteristics of the blend as desired.

The compositions described herein may also contain inorganic particulate fillers, which may improve the mechanical and wear properties of the compositions, particularly in compositions including crosslinked components. The amount of inorganic filler used is typically less than 60%, or less than 50%, or less than 40%, or less than 30%, based on the total weight of the composition. The inorganic fillers include particles less than 1 min. in diameter, rods less than 1 cm in length, and plates less than 0.2 $cm^2$ in surface area. Exemplary particulate fillers include carbon black, clays, titanium and magnesium oxides, and silica. In addition, other particulate fillers, such as calcium carbonate, zinc oxide, whiting, and magnesium oxide, can also be used. An example of a rod-like filler is glass fiber. An example of a plate-like filler is mica. The addition of very small particulate fibers, commonly referred to as nanocomposites, is also contemplated. The addition of the fillers may change the properties of the compositions described herein. For example, compositions including inorganic filler may have improved thermal stability and resistance to wear. The addition of white fillers may improve the temperature changes of the hydrocarbon polymers on exposure to sunlight. The addition of fillers beyond a certain level may lead to a dramatic increase in the viscosity and a corresponding decrease in processability. This threshold level is referred to as the percolation threshold. In addition to the increase in viscosity, the percolation threshold is accompanied by an improvement in the elastic properties, and at levels slightly higher than the percolation threshold there is a drop in the elastic recovery of the blend. The percolation threshold is attained at different levels of addition of fillers depending on the type of filler used. Generally, the percolation threshold is attained at lower levels for fillers with a smaller size than for fillers with a larger size.

The compositions described herein may contain process oil in the range of from 0 to 500 parts by weight, or from 2 to 200 parts by weight, or from 5 to 150 parts by weight, or from 10 to 100 parts by weight, per hundred parts of total polymer. The addition of process oil in moderate amounts may lower the viscosity and flexibility of the blend while improving the properties of the blend at temperatures near and below 0° C. It is believed that these potential benefits arise by the lowering of the glass transition temperature (Tg) of the blend. Adding process oil to the blend may also improve processability and provide a better balance of elastic and tensile strength. The process oil is typically known as extender oil in rubber applications. Process oils include hydrocarbons having either (a) traces of hetero atoms such oxygen or (b) at least one hetero atom such as dioctyl plithalate, ethers, and polyethers. Process oils have a boiling point to be substantially involatile at 200° C. These process oils are commonly available either as neat solids, liquids, or as physically absorbed mixtures of these materials on an inert support (e.g., clay, silica) to form a free flowing powder. Process oils usually include a mixture of a large number of chemical compounds which may consist of linear, acyclic but branched, cyclic, and aromatic carbonaceous structures. Another family of process oils are certain organic esters and alkyl ether esters having a molecular weight (Mn) less than 10,000. Combinations of process oils may also be used in the practice of the invention. The process oil should be compatible or miscible with the polymer blend composition in the melt, and may be substantially miscible in the propylene-alpha-olefin copolymer at room temperature. Process oils may be added to the blend compositions by any of the conventional means known in the art, including the addition of all or part of the process oil prior to recovery of the polymer, and addition of all or part of the process oil to the polymer as a part of a compounding for the interblending of the propylene-alpha-olefin copolymer. The compounding step may be carried out in a batch mixer, such as a mill, or an internal mixer, such as a Banbury mixer. The compounding operation may also be conducted in a continuous process, such as a twin screw extruder. The addition of process oils to lower the glass transition temperature of blends of isotactic polypropylene and ethylene propylene diene rubber is described in U.S. Pat. Nos. 5,290,886 and 5,397,832, the disclosures of which are hereby incorporated herein by reference.

The addition of process aids, such as a mixture of fatty acid ester or calcium fatty acid soap bound on a mineral filler, to the compositions described herein may help the mixing of the composition and the injection of the composition into a mold. Other examples of process aids are low molecular weight polyethylene copolymer wax and paraffin wax. The amount of process aid used may be within the range of from 0.5 to 5 phr.

Adding antioxidants to the compositions described herein may improve the long term aging. Examples of antioxidants include, but are not limited to quinolein, e.g., trimethylhydroxyquinolein (TMQ); imidazole, e.g., zincmercapto toluoyl imidazole (ZMTI); and conventional antioxidants, such as hindered phenols, lactones, and phosphites. The amount of antioxidants used may be within the range of from 0.001 to 5 phr.

Manufacture

Also provided are methods for making the compositions of the invention. In one embodiment, the invention encompasses a method for making a composition having pesticidal properties comprising the steps of: (1) forming a mixture comprising (a) a propylene-alpha-olefin copolymer comprising (i) at least about 50%, by weight of the propylene-alpha-olefin copolymer, of propylene-derived units and (ii) about 5% to about 35%, by weight of the propylene-alpha-olefin copolymer, of units derived from at least one of ethylene or a $C_{4-10}$ alpha-olefin, wherein the polypropylene-alpha-olefin copolymer has a heat of fusion of about 75 J/g or less, melting point of about 100° C. or less, and crystallinity of about 2% to about 65% of isotactic polypropylene; and (b) a condensation adduct of formula T1-T2, wherein T1 comprises at least one pyrethroid substantially stable up to a temperature of at least about 150° C. and T2 comprises an ethylenically unsaturated substance selected from at least one of a surfactant or vinyl phosphate, (2) heating the mixture, and (3) extruding the mixture.

In a preferred embodiment, the method comprises the steps of: (1) forming, such as by blending, a first mixture comprising (a) a first portion of the propylene-alpha-olefin copolymer; and (b) the condensation adduct of formula T1-T2; (2) heating the first mixture; (3) extruding the first mixture to form a masterbatch; and (4) blending the masterbatch with a second portion of the propylene-alpha-olefin copolymer or with a polyolefin such as polypropylene, polystyrene, low density polyethylene, high density polyethylene, or propylene-alpha-olefin copolymers.

In one embodiment, the invention relates to a method of forming a masterbatch comprising the steps of melt blending the propylene-alpha-olefin copolymer and the condensation adduct of formula T1-T2, and extruding the melt blend through at least one extruder die. In a preferred embodiment, the masterbatch comprises a polypropylene-alpha-olefin copolymer carrier, at least about 0.05%, by weight of the melt blend, of the condensation adduct of formula T1-T2, and preferably at least of about 0.05%, by weight of the melt blend, of at least one of a slip agent or an anti-blocking agent.

In one embodiment, the masterbatch is blended with a polyolefin such as polypropylene or high density polyethylene, and used to produce a film, filament, fiber, sheet, thermoformed or injection-molded article, woven or non-woven material, yarn, or netting such as a mosquito net.

Fiber

In one embodiment, the invention provides a fiber comprising a composition described herein. Methods for making the fibers of the invention include those which are well known to those of ordinary skill in the art. Fibers of the invention may have desirable softness and elastic properties and may be used in various applications, for example, continuous filament yarn, bulked continuous filament yarn, staple fibers, melt blown fibers, and spunbound fibers. In a particular aspect of this embodiment, fibers comprising a composition described herein may have one or both of the following advantages: 1) may be easily spun into fibers by extrusion through a spinneret followed by drawing to the desired denier, and 2) the ability to spin the fibers, as measured by the rate of spinning, may be unaffected across a wide blend composition range, even when the melt flow rate (MFR) of the blends is slowly decreased by the addition of the second polymer component to the propylene-alpha-olefin copolymer. The constancy of the spinning rate across a wide blend composition range is particularly unanticipated since the spinning rate is sensitive to the MFR of the polymer (or polymer blend), and low MFR polymers have poorer spinning performance.

In one embodiment, the invention provides fabrics made with the fibers of the invention. The fabrics may be made by any of the known processes for making non-woven or woven fabrics.

Film

In one embodiment, the invention provides a film comprising a composition described herein. Methods for making the films of the invention include those which are well known to those of ordinary skill in the art, including, but not limited to, conventional tubular extrusion, or a blown bubble process, and cast extrusion. The extrusion temperatures, die temperatures, and chill roll temperatures are dependent on the composition employed, but will generally be within the following ranges for the compositions described herein: melt temperature, 350° F. to 450° F.; die temperature, 350° F. to 450° F.; and chill roll temperature, 70° F. to 130° F. The film-making process may also include embossing rolls to chill and form the film.

The films of the invention may have a layer adhered to one or both sides of the inventive film. The layers may be adhered by coextrusion of the inventive film with the optional additional layer or layers. In coextruded films, the individual layers are different in composition and retain their composition except at the interface layer. The optional additional layer may be, for example, a soft material such as an ethylene propylene copolymer elastomer which may reduce the adhesive (i.e., sticky) feel of the inventive film. The optional additional layer may also be, for example, a thermoplastic. A thermoplastic layer may be used, for example, as a mechanical support for an elastic film to prevent sag, and as a barrier to adhesion of the polymer film to other surfaces. A thermoplastic layer may become a part of the integral use of an elastic film in that the composite film is stretched beyond the yield point of the thermoplastic layer, e.g., greater than 50% elongation, and allowed to retract due to the elastic forces of the elastic film. In this use, the thermoplastic film is wrinkled to yield a desirable surface finish of the composite elastic film. The thermoplastics that may be used for this purpose include, but are not limited to polypropylene and polyethylene.

Applications

The invention encompasses a film, filament, fiber, sheet, thermo-formed or injection-molded article, woven or non-woven material, yarn, or netting, such as a mosquito net, produced using the compositions or methods of the invention. Methods of their manufacturing are commonly known in the art and can be found, for example, in U.S. Pat. No. 4,241,123. In one embodiment, the invention encompasses nets, screens, or garments used to repel, disable, and/or kill insects such as mosquitoes. Examples include, but are not limited to, mosquito nets, bed canopies, beddings, sheets, pillowcases, head nets, window or door screens, curtains, tents, hammocks, blankets, sleeping bags, collars (e.g., for cattle, farm animals, or household pets), clothing (e.g., shirts, pants, jackets, gloves, scarves, and socks), swimwear, hats, and hiking, fishing or other outdoor gear.

The compositions of the invention including products made therefrom have pesticidal activity. These compositions and products are effective against pests such as, for example, flies, especially the housefly *Musca domestica*, mosquitoes, especially *Aedes aegypti*, lice, especially *Pediculus humanus capitis* (human head louse), *Pediculus humanus vestimenti* (human body louse), and *Phthirius pubis*, ants, cockroaches, and acarids, especially house dust mites *Dermatophagoides farinea* and *Dermatophagoides pteronyssinus*. The exact amount of pyrethroid to be used, depending on the pest to be controlled and the application of the final product, can be readily determined based on methods of known in the art. Typically, about 0.1% to about 0.5%, by weight of the final product, can be used against crawling pests, and about 0.5% to about 5% can be used against flying pests.

EXAMPLE

The following is a non-limiting example of a typical masterbatch composition.

| Component | Minimum % | Maximum % | Typical % |
|---|---|---|---|
| Cypermethrin-dichlorvos adduct | 10 | 38 | 25 |
| Vistamaxx 6202 (Propylene-alpha-olefin copolymer) | 55 | 90 | 65 |
| CROTAMID ™ (slip agent) | 0 | 11 | 5 |
| Sibelite ™ M4000 (anti-blocking agent) | 0 | 11 | 5 |

The following is a non-limiting example of a typical composition from which a mosquito net can be made.

| Component | Minimum % | Maximum % | Typical % |
|---|---|---|---|
| Cypermethrin-dichlorvos adduct | 0.3 | 1.1 | 0.7 |
| Vistamaxx 6202 | 0.5 | 3.0 | 1.8 |
| CROTAMID ™ | 0 | 0.6 | 0.15 |
| Sibelite ™ M4000 | 0 | 0.6 | 0.15 |
| Polyolefin | 96.0 | 99.0 | 97.2 |

All patents and patent applications, test procedures (such as ASTM methods), and other documents cited herein are fully incorporated by reference to the extent such disclosure is not inconsistent with this invention and for all jurisdictions in which such incorporation is permitted.

When numerical lower limits and numerical upper limits are listed herein, ranges from any lower limit to any upper limit are contemplated. While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

The invention has been described above with reference to numerous embodiments and specific examples. Many variations will suggest themselves to those skilled in this art in light of the above detailed description. All such obvious variations are within the full intended scope of the appended claims.

What is claimed is:

1. A fiber comprising a composition comprising:
   (a) a propylene-alpha-olefin copolymer comprising (i) at least about 50% by weight of the propylene-alpha-olefin copolymer of propylene-derived units and (ii) about 5% to about 35% by weight of the propylene-alpha-olefin copolymer of units derived from at least one of ethylene or a $C_{4-10}$ alpha-olefin, wherein the polypropylene-alpha-olefin copolymer has a heat of fusion of about 75 J/g or less, melting point of about 100° C. or less, and crystallinity of about 2% to about 65% of isotactic polypropylene; and
   (b) a pesticide.

2. The fiber of claim 1, wherein the pesticide is a pyrethroid.

3. The fiber of claim 2, wherein the pyrethroid is a condensation adduct of formula T1-T2, T1 comprises at least one pyrethroid substantially stable up to a temperature of at least about 150° C., and T2 comprises an ethylenically unsaturated substance selected from at least one of a surfactant or vinyl phosphate.

4. The fiber of claim 1, wherein the polypropylene-alpha-olefin copolymer has a melt flow rate of about 0.5 to about 100 dg/min.

5. The fiber of claim 1, wherein the propylene-alpha-olefin copolymer is present in an amount of about 60% to about 99.05% by weight of the composition.

6. The fiber of claim 1, wherein the condensation adduct of formula T1-T2 is present in an amount of about 0.05% to about 40% by weight of the composition.

7. The fiber of claim 1 further comprising a slip agent.

8. The fiber of claim 7, wherein the slip agent is present in an amount of about 0.01% to about 20% by weight of the composition.

9. The fiber of claim 1, further comprising an anti-blocking agent.

10. The fiber of claim 9, wherein the anti-blocking agent is present in an amount of about 0.05% to about 20% by weight of the composition.

11. The fiber of claim 2, wherein the pyrethroid is a compound of formula I:

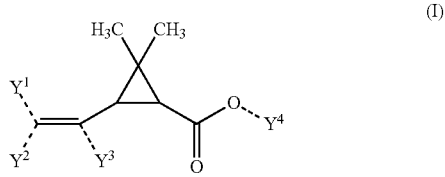

wherein $Y^1$, $Y^2$, and $Y^3$ may be the same or different and are hydrogen, halogen, or a $C_{1-40}$ hydrocarbon radical; and $Y^4$ is a $C_{1-40}$ hydrocarbon radical.

12. The fiber of claim 2, wherein the pyrethroid is (a) allethrin, cinerin, jasmolin, or pyrethrin, or (b) a compound of formula II:

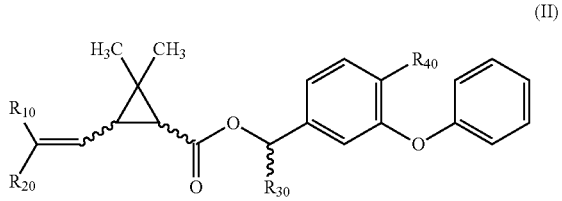

(II)

wherein $R^{10}$ and $R^{20}$ are the same or different and are H, F, Cl or Br; $R^{30}$ is H, CN, F, Cl, or Br; $R^{40}$ is H, OH, SH, F, Cl, or Br; and the symbol ∼∼∼ represents a bond having R or S configuration.

13. The fiber of claim 2, wherein the pyrethroid is deltamethrin, cypermethrin, cyhalothrin, or allethrin.

14. A fiber comprising a composition having pesticidal properties comprising:
   (a) about 60% to about 99.05% by weight of the composition of a propylene-alpha-olefin copolymer comprising (i) at least about 50% by weight of the propylene-alpha-olefin copolymer of propylene-derived units and (ii) about 5% to about 35% by weight of the propylene-alpha-olefin copolymer of units derived from at least one of ethylene or a $C_{4-10}$ alpha-olefin, wherein the polypropylene-alpha-olefin copolymer has a melt flow rate of about 0.5 to about 100 dg/min, heat of fusion of about 75 J/g or less, melting point of about 100° C. or less, and crystallinity of about 2% to about 65% of isotactic polypropylene;
   (b) about 0.05% to about 40% by weight of the composition of a condensation adduct of formula T1-T2, wherein T1 comprises at least one pyrethroid substantially stable up to a temperature of at least about 150° C. and T2 comprises an ethylenically unsaturated substance selected from at least one of a surfactant or vinyl phosphate;
   (c) about 5% to about 20% by weight of the composition of a slip agent; and
   (d) about 10% to about 20% by weight of the composition of an anti-blocking agent.

15. A method for making a composition having pesticidal properties comprising the steps of:
   (1) forming a mixture comprising (a) a propylene-alpha-olefin copolymer comprising (i) at least about 50% by weight of the propylene-alpha-olefin copolymer of propylene-derived units and (ii) about 5% to about 35% by weight of the propylene-alpha-olefin copolymer of units derived from at least one of ethylene or a $C_{4-10}$ alpha-olefin, wherein the polypropylene-alpha-olefin copolymer has a heat of fusion of about 75 J/g or less, melting point of about 100° C. or less, and crystallinity of about 2% to about 65% of isotactic polypropylene; and (b) a pesticide,
   (2) heating the mixture, and
   (3) extruding the mixture.

16. The method of claim 15 comprising the steps of:
   (1) forming a first mixture comprising (a) a first portion of the propylene-alpha-olefin copolymer; and (b) the pesticide,
   (2) heating the first mixture,
   (3) extruding the first mixture to form a masterbatch, and
   (4) combining the masterbatch with a second portion of the propylene-alpha-olefin copolymer or with a polyolefin selected from the group consisting of polypropylene, polystyrene, low density polyethylene, high density polyethylene, and propylene-alpha-olefin copolymers.

17. The method of claim 15, wherein the pesticide is a condensation adduct of formula T1-T2, T1 comprises at least one pyrethroid substantially stable up to a temperature of at least about 150° C., and T2 comprises an ethylenically unsaturated substance selected from at least one of a surfactant or vinyl phosphate.

18. The method of claim 15, further comprising the step of forming the composition into a film, a filament, a fiber, a sheet, a molded object, an extruded article, a woven or a non-woven material, a yarn, or a mosquito net.

19. A mosquito net, a bed canopy, bedding, sheets, a pillowcase, a head net, a window screen, a door screen, a curtain, a tent, a hammock, a blanket, a sleeping bag, a collar, clothing, swimwear, or a hat having pesticidal properties comprising the fiber of claim 1.

\* \* \* \* \*